United States Patent [19]
Stevens

[11] Patent Number: 5,810,000
[45] Date of Patent: Sep. 22, 1998

[54] ENDOTRACHEAL TUBE PACIFIER

[76] Inventor: Erin Stevens, 26071 Malaga La., Mission Viejo, Calif. 92692

[21] Appl. No.: 995,532

[22] Filed: Dec. 22, 1997

[51] Int. Cl.[6] .................................................. A61M 15/00
[52] U.S. Cl. ................................ 128/200.26; 128/200.24; 128/207.14; 606/234
[58] Field of Search ..................... 128/200.24, 200.26, 128/207.14, 207.15, 206.29, 202.16, DIG. 24, 911, 912, 207.17, 207.18; 606/234, 235, 236

[56] References Cited

U.S. PATENT DOCUMENTS

| | | | |
|---|---|---|---|
| 3,924,621 | 12/1975 | Cassimally | 128/252 |
| 5,004,473 | 4/1991 | Kalantar | 606/234 |
| 5,284,490 | 2/1994 | Green | 606/235 |

Primary Examiner—John G. Weiss
Assistant Examiner—Charles W. Anderson
Attorney, Agent, or Firm—Drummond & Duckworth

[57] ABSTRACT

An endotracheal tube pacifier is provided. The endotracheal tube pacifier includes a nipple portion, bite portion and flange portion. A slot is formed longitudinally along the length of the nipple portion, bite portion and flange portion of the endotracheal tube pacifier. The slot is configured to detachably receive the sidewalls of an endotracheal tube even when an extremity of the endotracheal tube has already been received within a patient's mouth. The endotracheal tube pacifier is intended to reduce the physical anomalies associated with prolonged endotracheal tube intubation and to promote the natural sucking and swallowing reflexes of an infant undergoing endotracheal intubation.

7 Claims, 2 Drawing Sheets

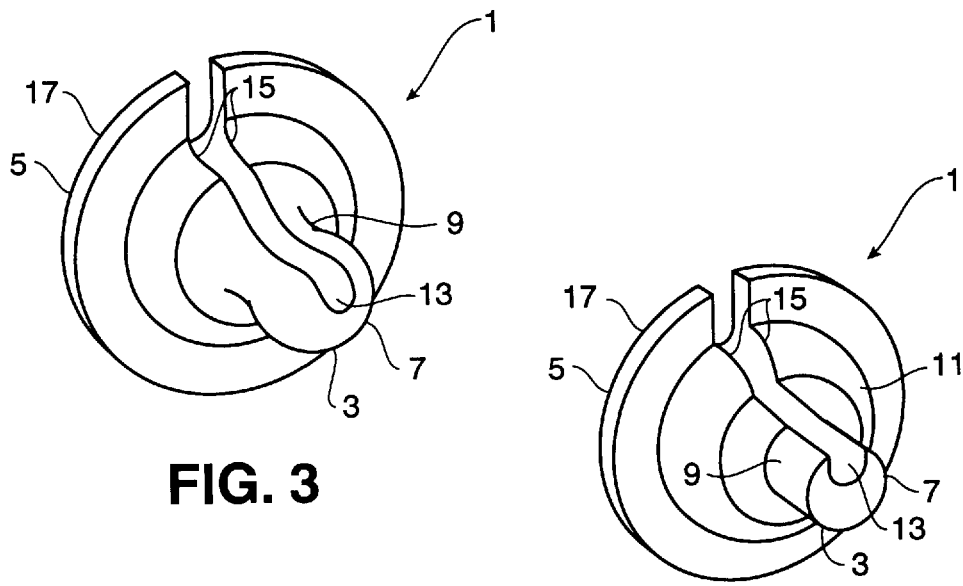
FIG. 3
FIG. 4
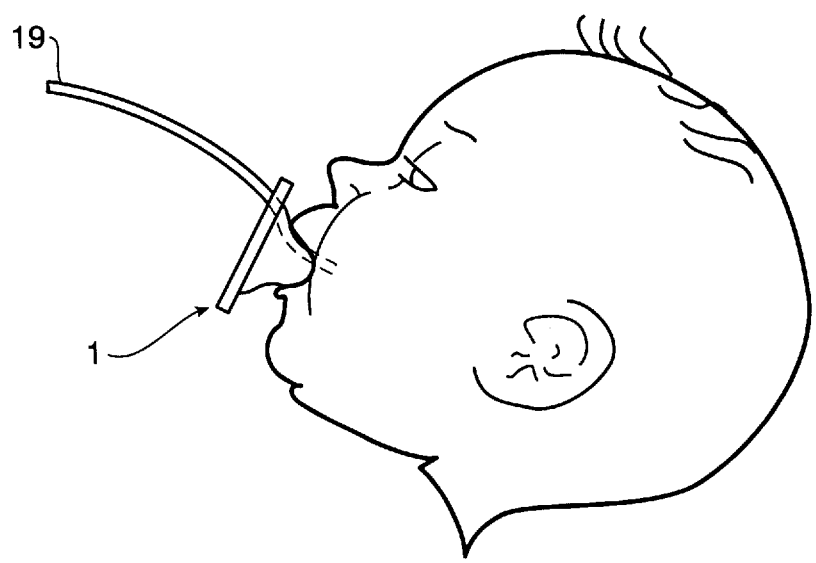
FIG. 5

ENDOTRACHEAL TUBE PACIFIER

BACKGROUND OF THE INVENTION

The present invention relates to endotracheal tubes.

Even more particularly, the invention concerns pacifiers for use with endotracheal tubes which are inserted orally into the trachea of an infant.

Endotracheal tubes are used to ventilate patients for recessitation, anesthesia, supplying oxygen and other critical care procedures. Infants that are in need of endotracheal intubation require that a tracheal tube pass through the babies mouth for entrance into the respiratory tract. Stabilizing and securing the endotracheal tube is also of vital importance. Traditionally, endotracheal tubes have been secured in place by attaching adhesive tape on the endotracheal tube and affixing the tape to the infant's face. Usually, the endotracheal tube is attached to the patient's upper lip by means of the adhesive tape.

Unfortunately, this procedure suffers from several disadvantages. Babies undergoing prolonged orotracheal intubation are more prone to various dental anomalies. For example, it has been shown that babies undergoing long exposure to orotracheal intubation are prone to narrowing, deepening and interior elongation of the infant's developing palate. Enamel hypoplasia has also been associated with oral intubation. Of particular concern is palatal grooving which is caused by prolonged pressure or rubbing of the tracheal tube against the infant's palate.

It is also been noted that babies, especially premature infants, try to suck on the orotracheal tube which can cause damage to the tooth buds thus causing later problems in gums, teeth and palates. Further, a failure prominent with the use of endotracheal tubes is accidental extubation.

An additional disadvantage of the present orotracheal intubation procedure is that it has been known to inhibit a babies natural propensity to suck. It is the natural characteristic of a baby to suck which calms the child. It also induces the production and secretion of digestive enzymes. However, it has been suggested that infants undergoing prolonged intubation do not develop normal sucking or a coordinated swallowing reflex.

Various attempts have been made to provide endotracheal tube pacifiers. For example, U.S. Pat. No. 5,146,913 issued to Khorsandian et al. discloses an orotracheal tube pacifier including a pacifier portion attached to a face plate which is secured to a patient's face and mouth by velcro straps. The tracheal tube must be extubated each time the pacifier is removed, and sanitized or replaced before insertion back into the infant's mouth. However, each insertion of the endotracheal tube into the patient's respiratory tract has been found to increase the risk of damage to the patient's throat, vocal chords, etc.

An additional attempt to reduce the dental anomalies of endotracheal intubation, and in an effort to promote an infant's natural propensity to suck, it has been known to insert a traditional pacifier into a patient's mouth adjacent to the orotracheal tube. Unfortunately, this procedure does not protect the infant's upper gums or pallet as the tracheal tube maintains contact with these portions of the infant's mouth. Accordingly, the patient is still prone to palatal grooving and other dental anomalies. Furthermore, the lack of coordination of the infant does not allow the infant to successfully suck on a pacifier while the orotracheal tube is in place.

It would be highly desirable to provide an endotracheal pacifier which can be removed and replaced without extubating the patient.

It would also be highly desirable to provide an endotracheal tube pacifier which would promote a baby's natural tendency to suck and coordinate the swallowing reflex.

It would also be highly desirable to provide an endotracheal tube pacifier which would reduce or eliminate the various dental anomalies associated with long exposure to endotracheal intubation.

SUMMARY OF THE INVENTION

Briefly, in accordance with the invention, I provide an endotracheal tube pacifier. The endotracheal tube pacifier includes a nipple portion, a bite portion and a flange portion. The nipple portion is curved and rounded to fit the palate of a patient in order to protect the patient from grooving or abrasion caused by the orotracheal tube alone. Proximal to the nipple portion of the endotracheal tube pacifier is the bite portion. The bite portion is curved or round in cross section and configured to engage a patient's lips, gums and teeth. As would be understood by those in the art, the nipple portion and bite portion are made of a resilient elastomeric material which is durable while non-damaging to a patient's mouth. The endotracheal tube pacifier further includes a flange portion which inhibits the pacifier from entering the patient's mouth. The flange portion extends proximally and radially from the bite portion of the endotracheal tube pacifier and has a sufficient radius as to not be easily received within the patient's mouth.

Extending longitudinally along the length of the nipple portion, bite portion and flange portion of the endotracheal tube pacifier is a slot. The slot is configured to receive an orotracheal tube along its length which is then held in place by means of a press-fit. In a preferred embodiment, the slot is approximately as deep as the diameter of the orotracheal tube so as to maintain the orotracheal tube substantially at the outer extremity of the pacifier when the pacifier is affixed to the orotracheal tube.

It is another feature of the present invention that the endotracheal tube pacifier be made of a resilient elastomer such as a rubber or soft plastic material. Further, it is preferred that the endotracheal tube pacifier be of a one-piece hollow construction.

It is an object of the present invention to provide an endotracheal tube pacifier which can be removed and replaced while an infant in intubated without having to remove the endotracheal tube from the child's passageways.

It is another object of the invention to provide a pacifier which promotes the natural sucking and swallowing reflexes of an infant.

It is still another object of the invention to provide an endotracheal tube pacifier which reduces or eliminates the physical anomalies which may result from prolonged endotracheal intubation.

These and other more specific objects and advantages of the invention will be apparent to those skilled in the art from the following detailed description taken in conjunction with the drawings.

BRIEF DESCRIPTION OF THE DRAWINGS

FIG. 3 is a perspective view of the endotracheal tube pacifier of the present invention including a spherical nipple;

FIG. 4 is a perspective view of the endotracheal tube pacifier of the present invention including an elongate cylindrical nipple; and FIG. 5 is a diagrammatic side view showing the endotracheal tube pacifier of the present invention in use.

DETAILED DESCRIPTION OF THE PREFERRED EMBODIMENTS

Figure 1:
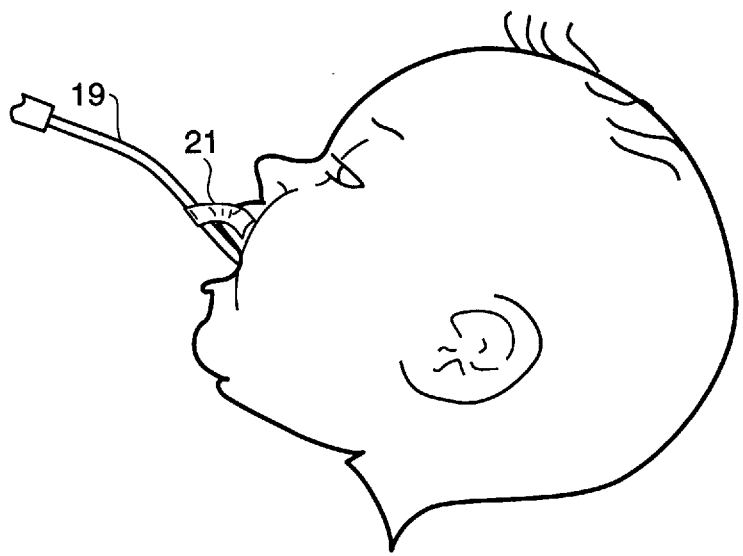
FIG. 1 is a side view showing a prior art intubation procedure.

While the present invention is susceptible of embodiment in various forms, as shown in the drawings, hereinafter will be described the presently preferred embodiments of the invention with the understanding that the present disclosure is to be considered as an exemplification of the invention and it is not intended to limit the invention to the specific embodiments illustrated.

Figure 2:
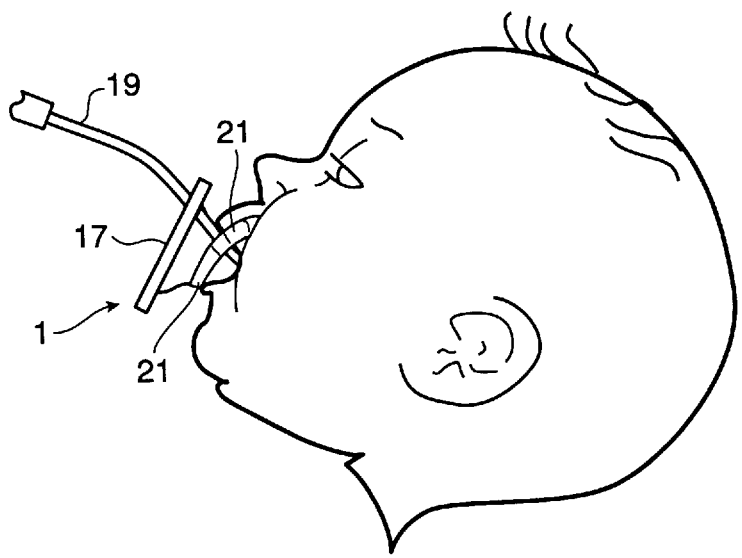
FIG. 2 is a side view showing a prior art intubation procedure including the use of a traditional pacifier.

As shown in FIG. 1, infants that are in need of orotracheal intubation must pass the tracheal tube 19 through the baby's mouth for entrance into the respiratory tract. The endotracheal tube is then affixed in place by medical tape 21 which is typically applied to the outer wall of the endotracheal tube and upper lip of the infant. The tape inhibits extubation; however, removal of the tape is painful to the infant. As shown in FIG. 2, medical practitioners have attempted to reduce the various dental anomalies associated with long exposure to endotracheal intubation by inserting a traditional pacifier into the infant's mouth adjacent to the endotracheal tube. The traditional pacifier is also thought to promote the child's natural propensity to suck which naturally induces the production secretion of digestive enzymes. The babies natural propensity to suck impels the traditional pacifier into the baby's mouth which, in turn, forces the tracheal tube against the baby's gums and pallet. The endotracheal tube pacifier of the present invention overcome the disadvantages of the prior art.

Referring to FIGS. 3–5, the endotracheal tube pacifier 1 of the present invention defines a distal extremity 3 which is intended to be received within a patient's mouth, and a proximal extremity 5 which is intended to remain outside the patient's mouth.

The endotracheal tube pacifier 1 includes a nipple portion 7, bite portion 9, and flange portion 11. Preferably, the nipple portion 7 is curved and rounded to engage the pallet and tongue of a patient. Furthermore, as understood by those in the art, the nipple may take numerous forms. For example, the nipple portion 7 may be substantially spherical with a diameter substantially greater than the diameter of the bite portion of the endotracheal tube pacifier (as shown in FIG. 3), or the nipple portion may be substantially cylindrical with a rounded distal extremity (as shown in FIG. 4).

The bite portion 9 of the endotracheal tube pacifier is curved or rounded in cross section and configured to engage a patient's lips, gums and teeth. Extending proximally from the bite portion 9 of the endotracheal tube pacifier 1 is the flange portion 11. The flange portion projects radially from the bite portion to form rear panel 17. The rear panel includes a diameter substantially greater than the diameter of the nipple portion 7 or bite portion 9 of the endotracheal tube pacifier 1 so as to be difficult to be received within the patient's mouth. More particularly, the diameter of the flange portion is sufficiently great so as to inhibit its receipt within the patient's mouth thereby preventing the patient from choking or swallowing the endotracheal tube pacifier.

The endotracheal tube pacifier 1 further includes a slot 13 formed longitudinally along the length of the nipple portion, bite portion and flange portion. In operation, the slot is configured to receive and affix an endotracheal tube along its length. In a preferred embodiment, the slot is approximately as deep as the diameter of the tracheal tube so as to maintain the endotracheal tube substantially at the outer extremity of the pacifier. Even more preferably, the inner walls 15 of the slot 13 maintain a press fit upon the endotracheal tube to lock the endotracheal tube in place and to restrict the endotracheal tube from sliding along the length of the pacifier's slot 13.

As shown in FIG. 5, the endotracheal tube is prevented from accidental extubation by the child's natural propensity to suck on the tracheal tube pacifier. More particularly, the endotracheal tube 19 is locked to the endotracheal tube pacifier 1 so that as the baby sucks on the pacifier, the endotracheal tube is restricted from sliding along the length of the pacifier slot 13 so as to accidentally exit the baby's mouth. Though not shown, medical tape may be applied to the endotracheal tube or pacifier and patient's face to provide an additional measure against accidental extubation.

Preferably, the endotracheal tube pacifier is made of a resilient elastomer such as a rubber or soft plastic material. Typical examples include polyolefin and silicone plastics. Further, it is preferred that the endotracheal tube pacifier be manufactured of a one-piece hollow construction.

Although particularly preferred embodiments of the present invention have been specifically described herein, it is to be understood that variations may be made in the construction, materials, and shape of the endotracheal tube pacifier without departing from the spirit scope of the invention. For example, as would be understood by those skilled in the art, the endotracheal tube pacifier is provided in different sizes depending on the age and physical characteristics of the patient. Further, the pacifier of the present invention includes slots of different depths and widths to accommodate endotracheal tubes of various diameters.

Having described my invention is such terms to enable those skilled in the art to make and use it, and having identified the presently preferred embodiment thereof, I claim:

1. An endotracheal tube pacifier having a distal extremity and a proximal extremity, the endotracheal tube pacifier comprising:
    a nipple portion having a curved and rounded configuration to fit and engage the palate and tongue of a patient;
    a bite portion extending proximally from said nipple portion and configured to fit and engage the teeth or gums of a patient;
    a radially projecting flange portion extending proximally from said bite portion and configured to engage the lips of a patient, said flange portion being of sufficient radius as to inhibit receipt of said flange portion into a patient's mouth; and
    a slot extending longitudinally along the length of said nipple portion, said bite portion and said flange portion and configured for receipt of an endotracheal tube, said slot disposed along the outer extremity of said pacifier to allow said pacifier to be engaged to an endotracheal tube and inserted into a patient's mouth or disengaged from an endotracheal tube and removed from a patient's mouth while the patient is intubated.

2. The endotracheal tube pacifier of claim 1 wherein said slot maintains the endotracheal tube substantially at the outer extremity of said pacifier while the patient is intubated.

3. The endotracheal tube pacifier of claim 1 further comprising a lock means for locking a endotracheal tube to said endotracheal tube pacifier.

4. The endotracheal tube pacifier of claim 3 wherein said lock means includes a press fit of said slot upon the outer walls of an endotracheal tube.

5. The endotracheal tube pacifier of claim 1 wherein the endotracheal tube pacifier is made of a resilient elastomer.

6. The endotracheal tube pacifier of claim 1 wherein said pacifier is of one-piece hollow construction.

7. The endotracheal tube pacifier of claim 1 wherein the nipple portion is substantially spherical in shape with a radius substantially greater than the radius of the bite portion to inhibit removal of the pacifier from a patients mouth.

* * * * *